(12) United States Patent
Alam et al.

(10) Patent No.: US 6,542,762 B1
(45) Date of Patent: *Apr. 1, 2003

(54) NEAR-INFRARED NONINVASIVE DETERMINATION OF PH IN PULSE MODE

(75) Inventors: Mary K. Alam, P.O. Box 1083, Cedar Crest, NM (US) 87008; Mark R. Robinson, 1415 Calle del Ranchero NE., Albuquerque, NM (US) 87106

(73) Assignees: Mary K. Alam, Albuquerque, NM (US); Mark R. Robinson, Albuquerque, NM (US)

( * ) Notice: Subject to any disclaimer, the term of this patent is extended or adjusted under 35 U.S.C. 154(b) by 36 days.

This patent is subject to a terminal disclaimer.

(21) Appl. No.: 09/587,478

(22) Filed: Jun. 5, 2000

Related U.S. Application Data

(63) Continuation of application No. 09/131,944, filed on Aug. 10, 1998, now Pat. No. 6,073,037, which is a continuation-in-part of application No. 08/615,762, filed on Mar. 14, 1996, now Pat. No. 5,792,050, which is a continuation-in-part of application No. 08/257,875, filed on Aug. 12, 1994, now Pat. No. 5,630,413, which is a continuation of application No. 07/910,004, filed on Jul. 6, 1992, now Pat. No. 5,355,880.

(51) Int. Cl.[7] ................................................. A61B 5/00
(52) U.S. Cl. .......................... 600/310; 600/322; 356/39
(58) Field of Search ................................. 600/309–310, 600/322–324, 326–327, 341–342, 336; 356/39–42

(56) References Cited

U.S. PATENT DOCUMENTS

| 4,041,932 A | 8/1977 | Fostick |
| 4,114,604 A | 9/1978 | Shaw et al. |
| 4,201,222 A | 5/1980 | Hasse |
| 4,324,256 A | 4/1982 | Vesterager |

(List continued on next page.)

FOREIGN PATENT DOCUMENTS

| EP | 453599 A1 | 10/1991 |
| EP | 522674 A2 | 1/1993 |

OTHER PUBLICATIONS

David M. Haaland, "Multivariate Calibration Methods Applied to Quantitative FT–IR Analyses," *Practical Fourier Transform Infrared Spectroscopy, Industrial and Laboratory Chemical Analysis*, J. R. Ferraro and K. Krishman, Academic Press, Inc., 1990.

(List continued on next page.)

*Primary Examiner*—Max F. Hindenburg
*Assistant Examiner*—Matthew Kremer
(74) *Attorney, Agent, or Firm*—DeWitt M. Morgan

(57) ABSTRACT

Methods and apparatus for, preferably, determining noninvasively and in vivo pH in a human. The non-invasive method includes the steps of: generating light at three or more different wavelengths in the range of 1000 nm to 2500 nm; irradiating blood containing tissue; measuring the intensities of the wavelengths emerging from the blood containing tissue to obtain a set of at least three spectral intensities v. wavelengths; and determining the unknown values of pH. The determination of pH is made by using measured intensities at wavelengths that exhibit change in absorbance due to histidine titration. Histidine absorbance changes are due to titration by hydrogen ions. The determination of the unknown pH values is performed by at least one multivariate algorithm using two or more variables and at least one calibration model. The determined pH values are within the physiological ranges observed in blood containing tissue. The apparatus includes a tissue positioning device, a source, at least one detector, electronics, a microprocessor, memory, and apparatus for indicating the determined values.

8 Claims, 12 Drawing Sheets

U.S. PATENT DOCUMENTS

| | | | |
|---|---|---|---|
| 4,509,522 A | | 4/1985 | Manuccia et al. |
| 4,685,465 A | | 8/1987 | Klitgaard et al. |
| 4,694,834 A | | 9/1987 | Meyerhoff et al. |
| 4,975,581 A | | 12/1990 | Robinson et al. |
| 4,989,606 A | | 2/1991 | Gehrich et al. |
| 5,103,829 A | | 4/1992 | Suzuki et al. |
| 5,197,470 A | * | 3/1993 | Heifer et al. ............... 600/342 |
| 5,222,495 A | * | 6/1993 | Clarke et al. ............... 600/322 |
| 5,355,880 A | * | 10/1994 | Thomas et al. ............. 600/326 |
| 5,630,413 A | * | 5/1997 | Thomas et al. ............. 600/310 |
| 5,792,050 A | * | 8/1998 | Alam et al. ................. 600/310 |
| 6,073,037 A | * | 6/2000 | Alam et al. ................. 600/310 |

OTHER PUBLICATIONS

J. F. O'Riordan, T.K. Goldstick, L.N. Vida, G.R. Honig, J.T. Ernest, "Modelling Whole Blood Oxygen Equilibrium: Comparison of Nine Different Models Fitted to Normal Human Data," *Advances in Experimental Medicine*, vol. 191, pp. 505–522. 1985.

E. Watson, E.H. Baughman, "On–Line Analysis of Caustic Streams by near–Infrared Spectoscopy," Spectroscopy, vol. 2, No. 1, pp. 44–48.

S.R. Goldstein, et al., "A Miniature Fiber Optic pH Sensor for Physiological Use," Journal of Biomechanical Engineering, May 1980, vol. 102, pp. 141–146.

B. Oeseburg et al., "Intravascular Ph–ISFET, a Method of the Future," Scand. J. Clin. Lab Invest., 1987 (47, Supp. 188; pp. 31–35.

P. Bergveld, "The Development and Application of FET–based Biosensors," Biosnesors, 1986, 2, pp. 15–33.

Drenne, et al., "Near–Infrared Spectrometric Determination of Hydrogen Ion, Glucose, and Human Serum Albumin in a Simulated Biological Matrix," vol. 6, No. 2, pp. 28, 30–34, 36.

M.K. Phelan, et al., "Measurement of Caustic and Caustic Brine Solutions by Spectroscopic Detection of the Hydroxide Ion in the Near–Infrared Region, 700–1150nm," Analytical Chemistry, 1989 61, 1419.

S.K. Soni and L.A. Kiesow, "pH–Dependent Soret Difference Spectra of the Deoxy and Carbonmonoxy Forms of Human Hemoglobin and Its Derivatives," Biochemistry, 16,1165–1170.

P.D. Wimberley, N. Fogh–Anderson, O. Siggaard–Andersen, F.C. Lundsgaard and W.G. Zijlstra, "Effect of pH on the Absorption Spectrum of Human Oxyhemoglobin: a Potential Source of Error in Measuring the Oxygen Saturation of Hemoglobin," Clinical Chemistry, 34, 750–754, 1988.

John S. Philo, Mary L. Adams, and Todd M. Schuster, "Association–dependent Absorption Spectra of Oxyhemoglobin A and Its Subunits," The Journal of Biological Chemistry, vol. 256, No. 15, Aug. 10, pp. 7917–7924, 1981.

Robin W. Brichl and Jean F. Hobbs, "Ultraviolet Difference Spectra in Human Hemoglobin," The Journal of Biological Chemistry, vol. 245, No. 3, Feb. 10, pp. 544–554, 1970.

Vasilis G. Gregoriou, Vasanthi Jayaraman, Xuehua Hu and Thomas G. Spiro, "FT–IR Difference Spectroscopy of Hemoglobins A and Kempsey; Evidence that a Key Quaternary Interaction Induces Protonation of Asp B99," Biochemistry, May 23, 1995, V. 34, No. 20, p. 6876.

D. Wedekind, U. Brunzel, R. Schweitzer–Stenner and W. Dreybrodt, "Correlation of pH–Dependent Resonance Raman and Optical Absorption Data Reflecting Haem–Apoprotein Interaction in Oxy Haemoglobin," Journal of Molecular Structure, vol. 143, pp. 457–460 (1986).

Anwendung einer CCD–Zeilen–Kamera zur Reflexions–spektroskopie im Blut Teil 1: Hamatokritunabhangige Sauerstoffsattigungsbestimmung dureh ein neues Auswertverfahrne published in Biomedizinissche Technik (1988) Okt., No. 10, W. Germany.

* cited by examiner

NEAR-INFRARED NONINVASIVE DETERMINATION OF PH IN PULSE MODE

This application is a continuation of application Ser. No. 09/131,944 filed on Aug. 10, 1998 (now U.S. Pat. No. 6,073,037), which is a continuation-in-part of Ser. No. 08/615,762 filed on Mar. 14, 1996 (now U.S. Pat. No. 5,792,050), which is a C-I-P of Ser. No. 08/257,875 filed Aug. 12, 1994 (now U.S. Pat. No. 5,630,413), which is a continuation of Ser. No. 07/910,004 filed Jul. 6, 1992 (now U.S. Pat. No. 5,355,880).

This invention is made with U.S. Government support and the U.S. Government has certain rights in this invention.

BACKGROUND OF THE INVENTION

This invention relates to both methodology and apparatus for the noninvasive determination of hydrogen ion concentration ($[H^+]$), commonly reported as -log ($[H^+]$) or pH in tissue.

Current methodology for blood pH measurement requires blood samples to be measured using a sophisticated blood analyzer equipped with electrodes to measure the desired analyte. Standard analyzer instrumentation (such as supplied by Ciba Coming, Abbot Laboratories and Radiometer) automates sample preparation, delivery, and measurement. After each sample is analyzed, the electrodes must be thoroughly washed to prevent protein buildup on the electrode surfaces, and the analyzer must be calibrated at a minimum of every two hours. Measurement of pH, along with other blood analytes (i.e., $PCO_2$, $[HCO_3^-]$, $PO_2$ and $O_2$ sat.), can be made with these analyzers in approximately two minutes. However, due to the size and expense of commercially available blood analyzers, such equipment is kept in central locations in most hospitals, requiring the blood sample to be transported to the analyzer.

While an individual analysis can be made in a few minutes, for an individual patient (often critically ill) the process is far from continuous and, because it is invasive, not without discomfort or pain. First, arterial blood has to be withdrawn. Immediately after withdrawal, the sample is placed on ice to inhibit red blood cell metabolism, which metabolism would alter the sample's blood gas parameters and lead to an incorrect measurement of the patient's blood gas values (including pH). The sample is then, typically, transported to the clinical chemistry laboratory in the hospital, where it is logged in. Next, the sample is then analyzed by conventional electrochemical techniques with the type of equipment identified above. Finally, the results are entered in the hospital computer and made available to the physician for interpretation. Thus, the analysis can require a significant period of time (approximately 30 minutes) during which patient status can change.

Localizing pH measurement to treatment rooms, with the use of reagentless measurement of pH, would allow for semi-continuous measurement. This decrease in turnaround time for pH measurement would, in turn, provide the clinician better evaluation of treatment methods. While such improvements in pH measurement could be realized with in-vitro optical methodologies, greater gains can be realized with the noninvasive, in-vivo methodology as disclosed herein.

Several groups have published papers on the spectroscopic effects of pH variation on blood, primarily related to the Bohr effect. See, S. K. Soni and L. A. Kiesow, "pH-Dependent Soret Difference Spectra of the Deoxy and Carbonmonoxy Forms of Human Hemoglobin and Its Derivatives," Biochemistry, 16, 1165–1170, 1977, wherein the authors reported seeing variation in the Soret absorption bands of hemoglobin (i.e., 350–400 nm) with pH. These spectral variations were ascribed to structural changes in the porphyrin of hemoglobin, caused by pH variation. Other researchers have found that the visible absorption bands (i.e., 400–550 nm) from oxyhemoglobin have a pH sensitivity. See P. D. Wimberley, N. Fogh-Andersen, O. Siggaard-Andersen, F. C. Lundsgaard and W. G. Zijlstra, "Effect of pH on the Absorption Spectrum of Human Oxyhemoglobin: a Potential Source of Error in Measuring the Oxygen Saturation of hemoglobin," Clinical Chemistry, 34, 750–754, 1988. Wimberley and coworkers did not attribute these spectral changes to the known variation in oxygen affinity caused by pH variation (i.e., Bohr effect). Rather, the variations seen were attributed to changes in the surrounding globin structure of the hemoglobin molecules, giving rise to changes in the charge-transfer bands of the porphyrin.

In the mid-infrared region (i.e., from approximately 2500 nm–10,000 nm), work has been done to determine the effects of pH variation on the vibrational modes of hemoglobin. In-vitro experiments with pure hemoglobin have shown that certain vibrational modes of the globins, in particular, the sulfur-hydrogen (S—H) stretching vibration of two cysteinyl ($\alpha$Cys104, $\beta$Cys112) are strongly hydrogen bonded and are sensitive to slight conformational changes of oxyhemoglobin caused by pH variation. See S. E. Antri, O. Sire and B. Alpert, "Relationship Between Protein/Solvent Proton Exchange and Progressive Conformation and Fluctuation Changes in hemoglobin," Euro. J. Biochem., 191, 163–168, 1990. These S—H vibrational modes were used to study the quaternary and tertiary structure of the hemoglobin molecule. However, from a clinical standpoint the mid-IR region is not useful because of the very high absorption of these wavelengths by tissue (i.e., there is no return signal from the tissue).

The near infrared region (i.e., from approximately 500 to 2500 nm) has been an active area of research for those pursuing non-invasive detection of blood analytes. Significant research has been done in the areas of oxygen saturation and glucose monitoring. See: (1) D. M. Haaland, M. R. Robinson, G. W. Koepp, E. V. Thomas and R. P. Eaton, "Reagentless Near-infrared Determination of Glucose in Whole Blood Using Multivariate Calibration," Appl. Spec., 46, 1575–1578, 1992; (2) B. Chance, J. S. Leigh, H. Miyake, D. S. Smith, S. Nioka, R. Greenfeld, M. Finander, K. Kaufman, W. Levy, M. Young, P. Cohen, H. Yoshioka and R. Boretsky, "Comparison of Time-Resolved and -Unresolved Measurements of Deoxyhemoglobin in Brain," Proc. Natl. Acad. Sci., 85, 4971–4975, 1988; (3) M. A. Arnold and G. W. Small, "Determination of Physiological Levels of Glucose in an Aqueous Matrix with Digitally Filtered Fourier Transform Near-Infrared Spectra," Anal. Chem., 62, 1457–1464, 1990; (4) Y. Mendelson and M. V. Solamita, "The Feasibility of Spectrophotometric Measurements of Arterial Oxygen Saturation from the Fetal Scalp Utilizing Noninvasive Skin-Reflectance Pulse Oximetry," Biomedical Instrumentation & Technology, May/June, 215–224, 1992; (5) U.S. Pat. No. 4,975,581 to Robinson, et al.; and (6) U.S. Pat. No. 5,492,032 to Robinson, et al. The lowered extinction coefficients (e.g., the size or intensities of the bands) and decreased scatter coefficients in the near-infrared region affords a much greater penetration depth (i.e., 1–10 mm) into human tissue than the visible or mid-infrared regions. In the near-infrared, absorbances are primarily due to overtone and combination bands of fundamental stretching and bending vibrations, although some low lying electronic transitions appear at the shorter wavelengths. The strongest near infrared bands will arise when there is a strong asymmetry in the fundamental mode, such as exists with N—H, O—H and C—H vibrational modes, thus making these species the primary absorbers in the near infrared.

U.S. Pat. No. 5,355,880 to Edward V. Thomas, Mark R. Robinson, David M. Haaland and Mary K. Alam titled "Reliable Noninvasive Measurement of Blood Gases" (hereinafter "Thomas et al.") discloses methods and apparatus for determining noninvasively and in vivo at least two of the five blood gas parameters (i.e., pH, $PCO_2$, $[HCO_3^-]$, $PO_2$ and $O_2$ sat.) in a human. The noninvasive methodology disclosed includes the steps of: generating light at three or more different wavelengths in the range of 500 nm to 2500 nm; irradiating blood containing tissue; measuring the intensities of the wavelengths emerging from the blood containing tissue to obtain a set of at least three spectral intensities v. wavelengths; and determining the unknown values of at least two of pH, $[HCO_3^-]$, $PCO_2$ and a measure of oxygen concentration. The determined values were found to be within the physiological ranges observed in blood containing tissues. The methodology disclosed also includes the steps of providing calibration samples, determining if the spectral intensities v. wavelengths from the tissue represents an outlier, and determining if any of the calibration samples represents an outlier. The determination of the unknown values was performed by at least one multivariate algorithm (e.g., PLS (partial least squares), PCR (principal component regression) and CLS (classic least squares) using two or more variables and at least one calibration model. Preferably, there is a separate calibration for each blood gas parameter being determined. The methodology can be utilized in a pulse mode and can also be used invasively. The apparatus disclosed by Thomas et al. includes a tissue positioning device, a source, at least one detector, electronics, a microprocessor, memory, and apparatus for indicating the determined values.

The rationale of Thomas et al. for using multivariate analysis for noninvasive blood gas determination is to enable accurate determination of blood gas parameters where the information content in the spectral domain utilized overlaps and where the infrared patterns for pH, $PCO_2$, $PO_2$ and $[HCO_3^-]$ are small or do not exist in the absence of interactions with water and other blood or tissue components. This is especially true for pH which does not exhibit a strong correlation in any specific region. Thomas et al. also observed that not only does water have exceptionally strong absorption bands in the near infrared region, but $H^+$ and $O_2$ have no absorption bands of their own in the near infrared.

Thomas, et al., disclose the measurement of arterial blood gases on a lamb through the use of a Si array detector and a grating spectrometer. The spectra acquired were over the 500–1000 nm range. Thomas, et al., at col. 28, //. 28–35, went on to state:

Although the data used to demonstrate proof of concept in the lamb study was recorded from 500 to 1000 nm, this is not the only frequency region of interest. Specifically, the region from 1000 nm to 2400 nm contains information on both hydrogen ion concentration and $CO_2$, (E. Watson and E. H. Baughman, *On-line analysis of caustic streams by near-infrared spectroscopy.* Spectroscopy, Vol. 2, No. 1, pp. 44–48.

In the reference by E. Watson, et al., the spectroscopic variations due to the varying hydrogen ion levels are due to changes in the water absorption bands. In summary, Thomas, et al., observed that hydrogen ion, being an ion rather than a molecule, does not have infrared bands. However, hydrogen ions will bind to other species in solution that are infrared active, thus a correlation for pH can be based on secondary spectroscopic effects. In the wavelength region of 1000–2500 nm, Thomas, et al., do not specify the exact source of the spectroscopic information for pH measurements in blood and no figures were provided disclosing the spectroscopic bands of importance.

In this application, the dominant source of spectroscopic information for pH measurement in blood in the 1000–2500 nm is identified, figures are provided demonstrating the relevant spectroscopic features, and the source of spectroscopic information is found to be different than identified by E. Watson.

It is an object of the invention to determine pH both in blood and in human tissue, utilizing spectral data from histidine in the range of 1000–2500 nm.

It is an object of the present invention to determine pH, both in blood and in human tissue, utilizing the spectral data from histidine in one or more of the ranges: 1000–1300 nm; 1500–1820 nm; 2040–2380 nm; and 1300–2380 nm.

It is a further object of the present invention to determine pH, both in blood and in human tissue, utilizing spectral data from histidine at, approximately, one or more of the following wavelengths: 1042 nm; 1111 nm; 1163 nm; 1600 nm; 2060–2115 nm; 2160 nm; 2225–2235 nm; and 2360 nm.

It is a further object to determine pH in pulsatile blood in a human.

A further object of the present invention is to provide a methodology, and associated apparatus, for determining pH, in blood and in human tissue, with standard errors or prediction below 0.05 pH units for a pH range of 1 (i.e., 6.8–7.8).

SUMMARY OF THE INVENTION

This invention relates to methodology and apparatus for determining noninvasively and in vivo pH in humans utilizing tissue spectra which spectra contains histidine information. The method includes the steps of generating light at three or more different wavelengths, the wavelengths being in the range of 1000 nm to 2500 nm; noninvasively irradiating blood containing tissue with the wavelengths so that there is differential attenuation of at least some intensities of the wavelengths, the wavelengths dependent differential attenuation being an function of the blood containing tissue, including histidine in the blood containing tissue; measuring the intensities of the wavelengths emerging from the blood containing tissue to obtain a set of at least three spectral intensities v. wavelengths; estimating the value of the pH from the intensities emerging from the blood containing tissue by utilizing wavelength dependent differential attenuation derived from the histidine, the value being within the physiological ranges observed in blood containing tissue. The method utilizes wavelength dependent differential attenuation derived from histidine which exhibits a sensitivity due to changes in pH. The wavelengths used for the estimation of pH are those known to exhibit a differential attenuation due to hydrogen ions reacting with histidine. The wavelengths are in the range of 1000–2500 nm. In the 1000–2500 nm region, wavelengths include one or more of 1042, 1111 and 1163 nm. In the range of 1500–1820 nm, wavelengths include 1600 nm. Finally, in the range of 2040–2500 nm the wavelengths include one or more of 2060–2115, 2160, 2225–2235 and 2360 nm.

A quantitative analysis instrument for noninvasive spectroscopic measurement of pH in human tissue includes: a source of at least three different wavelengths of light, the wavelengths being in the range of 1000–2500 nm, at least some of the wavelengths having a wavelength dependent differential attenuation due to histidine; optics for directing the wavelengths of light into the blood containing tissue; at least one detector for measuring the intensity of at least a portion of those of the wavelengths of light emerging from the blood containing tissue that are differentially attenuated by histidine; electronics for processing the measured intensities to estimate pH values in tissue; and apparatus for indicating the estimated values of blood pH. The electronics utilizes a multivariate algorithm using at least two variables and a calibration model. The algorithm is capable of using more spectral variables per sample than the number of calibration samples used to generate the model, and wherein each of the variables consists of at least one measured spectral intensity.

The invention also relates to methodology and apparatus for determining in vitro pH in blood utilizing spectra which spectra contains histidine information.

DESCRIPTION OF THE PREFERRED EMBODIMENT

Figure 1:
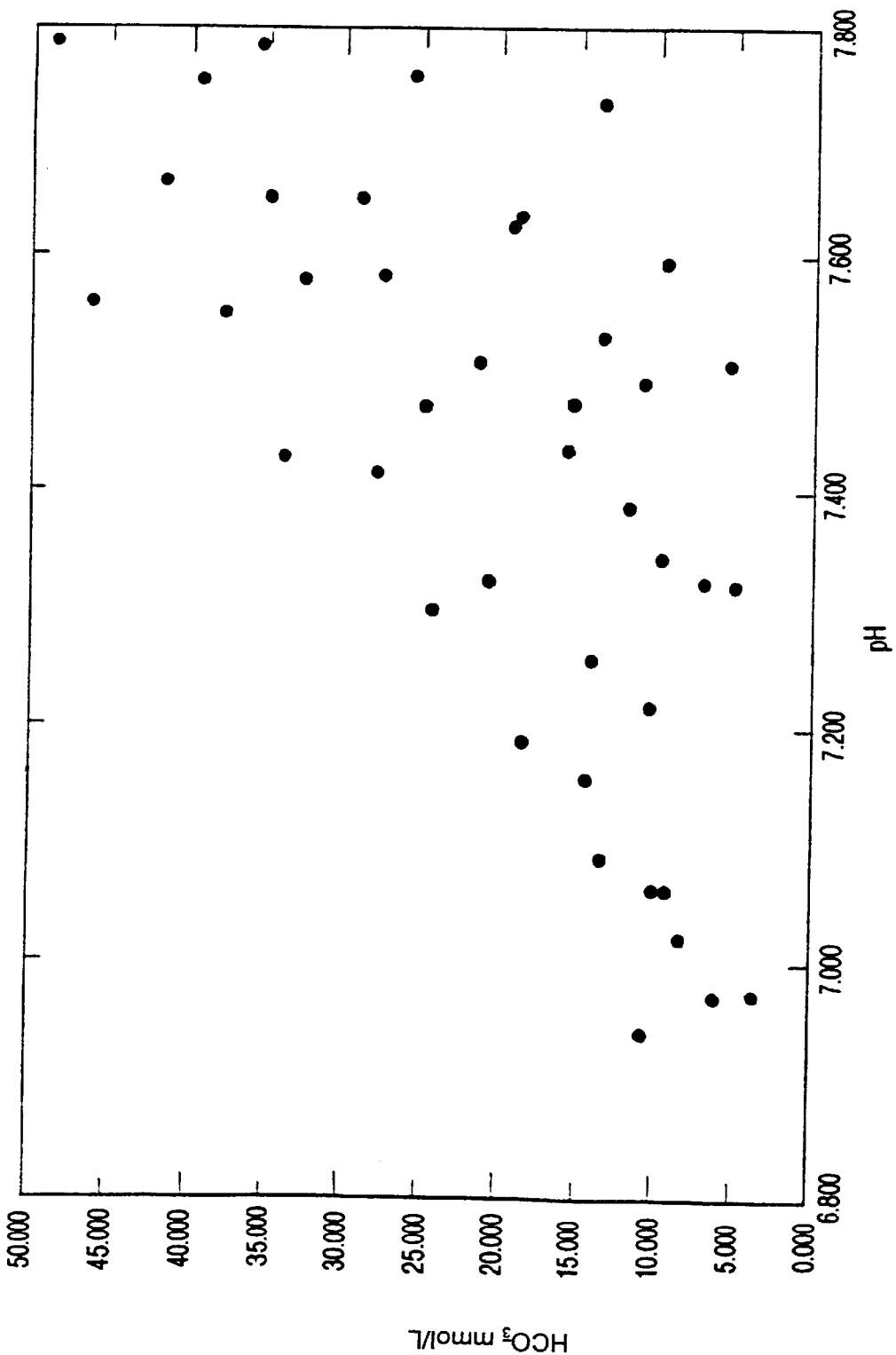
FIG. 1 illustrates how the relationship between pH and [$HCO_3^-$] is minimized with $PCO_2$ varying between 5 and 50 mmHg.

As discussed above, spectroscopic detection of pH variation is dependent on a sensitive and appropriate indicator species. In blood, there are four main systems responsible for buffering (i.e., combining with hydrogen or hydroxyl ions while maintaining a constant pH): hemoglobin; bicarbonate; plasma proteins; and phosphate. Each of these was considered as the source of pH signal during the examination of lysed blood discussed below. Phosphate buffers are minimal in their buffering capacity, are in low concentration, provide essentially no signal in the near-infrared and, thus, were eliminated as a possible spectral source of pH information. Plasma proteins, while in significant concentration, do not provide a large variation in spectral signal to be a sufficient indicator species for pH. Support for this comes from the near-infrared spectra examined, which indicated only minimal correlation with pH. Titration data supports this finding. See, C. Tanford, S. A. Swanson and W. S. Shore, "Hydrogen Ion Equilibria of Bovin Serum Albumin," J. Amer. Chem. Soc., 77, 6414–6420, 1955.

The bicarbonate buffer is not an appropriate indicator species for spectroscopic determination of pH. The relationship between bicarbonate ion and pH is defined by the chemical equilibrium:

$$CO_2 + H_2O \leftrightarrows H_2CO_3 \leftrightarrows HCO_3^- + H^+$$

Thus, at constant $CO_2$, bicarbonate ion concentration is correlated pH through a simple logarithmic function and any spectroscopic variation due to bicarbonate would be modeled as pH variation. Any variation in $CO_2$ content would break the correlation between bicarbonate and pH, causing a pH model based on bicarbonate concentration to predict erroneously. Perhaps more important is the clinical distinction between pH and bicarbonate measurements. Delineation of differing types of alkalosis and acidosis are decided based on the relationship between pH, $HCO_3$ and $CO_2$ values. Thus, spectroscopic models for pH must not derive information from the spectroscopic variation in bicarbonate concentration. As discussed below, this is achieved by choosing the calibration points in order to optimize orthogonality between pH and [$HCO_3^-$]. In this manner, it is certain that if the bicarbonate ion has a spectroscopic signature, it will vary orthogonally to the signature for pH and will not adversely affect the final pH model.

The hemoglobin buffer system is the largest component of the blood's buffering capacity, making it appropriate to use as an indicator species. Hemoglobin derives its buffering capacity from histidine throughout the molecule. It is known that variation in pH will cause a change in the tertiary structure of hemoglobin causing a corresponding change in oxygen binding. Several amino acids which reside at the globin chain interfaces are thought to be largely responsible for this structure change, including histidine. Because of this, we have determined that, for robust spectroscopic model development, it is necessary to break the direct correlation of hemoglobin oxygen saturation to pH. To achieve this, we titrated the so-called "Bohr protons", causing the subsequent structure changes in the hemoglobin molecule. However, we avoided making the spectroscopic model dependent on hemoglobin oxygen saturation through the use of the statistical design set forth below.

To demonstrate that pH in human tissue can be accurately determined utilizing spectral data from histidine in the range of 1300–2500 nm, fresh human blood, 500 ml, was collected from a healthy, nonsmoking volunteer. An anticoagulant heparin ($\approx 0.2$ g/ml) was then added. The red blood cell walls were ruptured by sonicating 40 ml aliquots (i.e., portions) of the blood using a sonication probe. The blood was kept in ice water during the sonication process. The resulting solutions were centrifuged at 3000 rpm and 10° C. Supernatant from each of the solutions was removed, combined and used for sample preparation. Cell walls were discarded.

Figure 2:
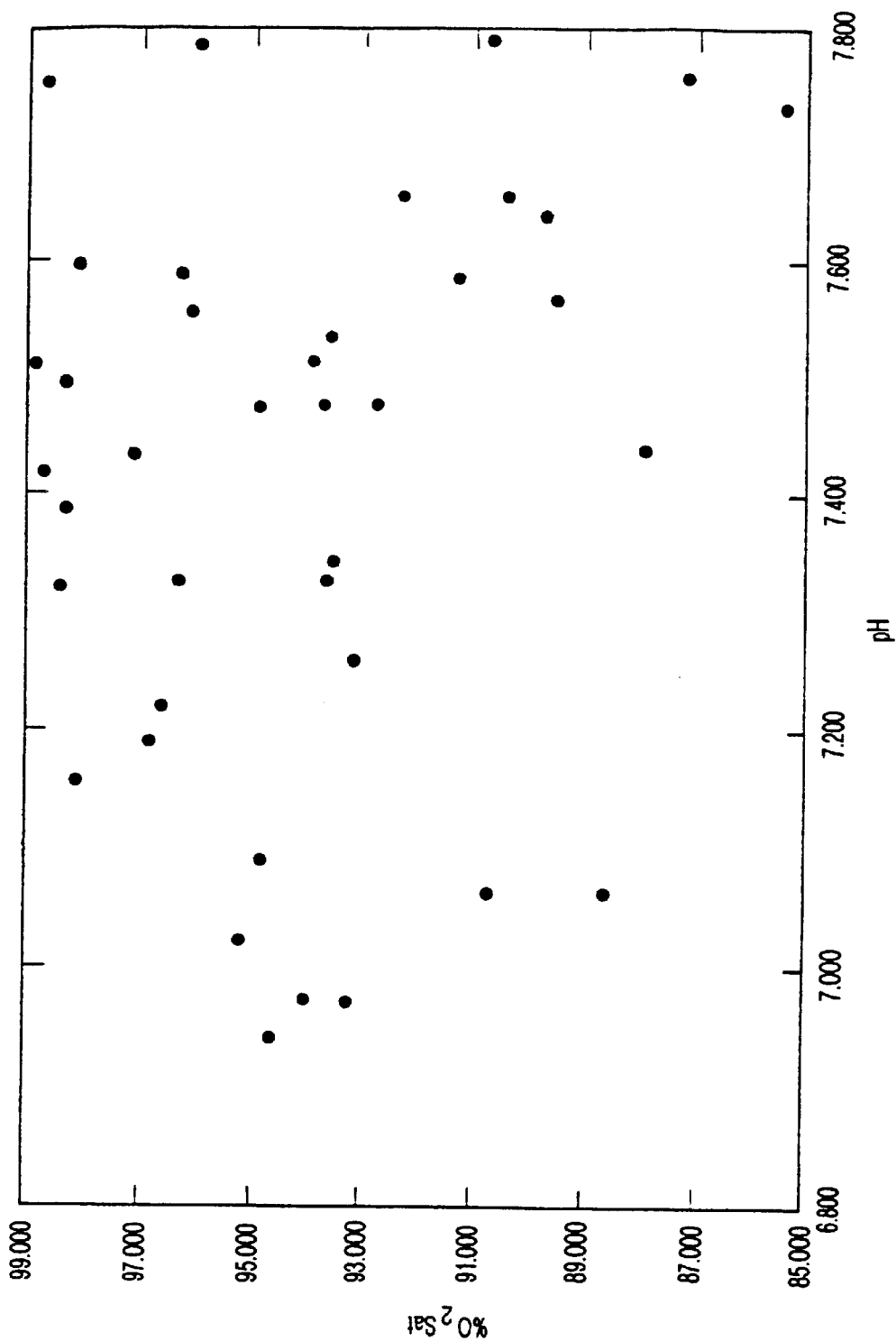
FIG. 2 illustrates how the correlation between pH and $O_2$ sat is minimized by varying $PO_2$.

To avoid the development of spectroscopic models for pH based on spurious and unreliable correlations, it is necessary to insure orthogonality between pH, [$HCO_3^-$] and $O_2$ sat. This was achieved using a Latin Hypercube with D-optimality criterion (i.e., a statistical design that minimizes the possibility of results based on spurious correlations). Forty-three (43) target points were developed. In order to break the correlation between pH and [$HCO_3^-$], the partial pressure of $CO_2$ was varied. $PCO_2$ values were limited to a physiological range of 5–50 mmHg, thus limiting the achievable values for [$HCO_3^-$] at a given pH to 5–50 mmol/L. The relationship between pH and $O_2$ sat. was broken through variation of the partial pressure of oxygen ($PO_2$) between 22 and 480 mmHg. By using the foregoing nearly orthogonal design, correlation between pH and [$HCO_3^-$], as well as pH and $O_2$ sat., was minimized. The results are illustrated in FIG. 1 (which illustrates the relationship between pH and [$HCO_3^-$] for the lysed blood) and FIG. 2 (which illustrates the relationship between pH and $O_2$ sat. for the lysed blood).

Forty-three (43) samples of the above identified lysed blood were prepared for analysis by spectroscopy. Each sample was a mixture of approximately 5 mls lysed blood, and 2 mls of a saline mixture. The absolute amount of lysed blood used in the mixture was adjusted in order to obtain a hemoglobin concentration of 10 g/dL in each of the final samples. The saline mixture consisted 0.9% (weight) NaCl and either HCl or NaOH the choice and amount of which depended on the desired blood gas values. The amount of acid or base required was estimated using the Sigaard-Anderson equation for base excess, $$\text{Base Excess}=(1-0.014[Hb])\{([HCO_3^-]-24)+(9.5-1.63[Hb])(pH-7.4)\}$$

where [Hb] is the hemoglobin concentration in g/dL and [$HCO_3^-$] is the bicarbonate ion concentration in mmol/L. Base excess estimates the amount of acid or base needed to titrate blood to a normal acid base status (pH=7.40, $pCO_2$=40 mmHg, Hb=15 g/dL, temperature=37° C.).

Each of the 43 solutions was prepared by weight. Once mixed, each solution was equilibrated for 10 minutes with a humidified mixture of $N_2$, $O_2$ and $CO_2$ (Air Liquide, local distributor) using an IL Instruments tonometer, model 237. Humidification is needed to prevent desiccation of the solutions. The samples were maintained at 37° C. (approximately normal human body temperature) while in the tonometer. $N_2$, $O_2$ and $CO_2$ mixtures for the tonometer were set using a Cameron Instruments (Port Aransas, Tex.) mass flow controller, model GF-3. Component ranges were 6.8–7.8 for pH, 5–50 mmol/L for [$HCO_3^-$] and 85–100% for $O_2$ sat.

Once prepared, each sample was, with apparatus 11 (see FIG. 3), infused into a flow system that allowed for spectroscopic sampling. The flow system consists of a syringe pump 13 (Harvard Apparatus, South Natick, Mass.) and a 1 mm spectroscopic cell 15 connected by stainless steel tubing 17. Blood gas parameters pH, $pCO_2$, and $PO_2$ were measured (offline) prior to and after spectroscopic measurement using a Corning model 288 automated blood gas analyzer. No significant difference was noted between the two offline ABG measurements. Flow was maintained at 2 ml per minute to insure that flow cell 15 remained full for 2 minutes, and to allow a 2 minute spectral acquisition which provided a low noise signal. Prior to each new sample, the flow system was cleaned using water, bleach and a detergent solution. The entire flow path, excluding the syringe pump 13, cell 15, tubing 17, and a waste container (not shown), is enclosed in a temperature controlled box 19 maintained at 37° C.

The spectral data used for the analysis described below was obtained from Nicolet Magna 750 FTNIR spectrometer 21 configured for external sampling. A 2 mm liquid nitrogen cooled InSb detector 23 was used to collect light after transmission through the 1 mm path length of flow cell 15. Spectrometer 21 and detector 23 are optically interconnected by conventional optics, including lenses 25, 27, 29, 31 and 33. The light source 35 is a stabilized tungsten halogen source.

For each of the 43 samples, 356 spectral interferograms were collected via FTIR data acquisition accessories 37 and 39 and transformed to single beam scans using a DEC station 3000 (work station 41). The resulting single beam scans were coadded resulting in one single beam spectrum for each of the 43 samples. Absorbance data were calculated using the resulting single beam spectra and the spectrum of cell 15 (when empty) as the background. The coadditions and absorbance calculations were performed using personal computer 43. After cutting off wavelengths from 2400–2500 nm (because of high noise), the resulting spectral data covered the range 1300–2400 nm with an approximate resolution of 3 nm (16 cm−1). Solutions were run in a random manner with respect to the component (i.e., pH, [$HCO_3^-$], and $O_2$ sat) concentrations in order to avoid correlation with instrument drift. For each of the 43 spectra, 356 interferograms were coadded. Of the 43 spectra collected, 39 were used for further analysis. The remaining four spectra were not included in the analysis because they had associated component values significantly different from expected target values, putting them outside the desired component ranges (i.e., outliers).

For comparison with the data outlined above from lysed blood and to demonstrate the relationship between pH in tissue and histidine, a 200 mmol/L solution of histidine (Sigma Chemical) was prepared in saline (0.9 wt % NaCl) and titrated. Forty-four solutions were prepared spanning the pH range 5–8. The pH of each solution was measured using a glass electrode (Orion Research) and near infrared spectra immediately collected. Solutions were placed in a 10 mm quartz cell and placed in the sample compartment of a Bomem MB-155 FTNIR spectrometer equipped with a InAs thermoelectrically cooled detector. Samples were run in a random order to prevent spurious correlation to run order. Spectra of the empty cell were collected and used for processing the solution spectra to absorbance.

Finally, and again for comparison with the data obtained above from lysed blood and to demonstrate that plasma proteins are not a significant indicator species for pH, fresh frozen plasma was obtained from United Blood Services (Albuquerque, N. Mex.). Once thawed, the plasma solution was centrifuged to remove any precipitated proteins. The protocol described above for the lysed blood samples was used for preparation of the plasma samples (except for sonication). Forty-three samples were prepared using the same procedure as used for the lysed blood. Spectra were collected using the apparatus illustrated in FIG. 3. Interferograms collected were processed to absorbance data prior to mathematical modeling.

With the spectroscopic data obtained above for the lysed blood, histidine and plasma, mathematical modeling (via personal computer 43) was employed to identify the spectral regions where pH can be predicted at clinically useful accuracies and that histidine provides the necessary variation for pH modeling. PLS modeling was performed using software developed at Sandia National Laboratories. PLS is a quantitative multivariate calibration technique which models the covariance of the spectral intensities with the reference values of the analyte. See, D. M. Haaland and E. V. Thomas, "Partial Least-Squares Methods for Spectral Analysis. 1. Relation to Other Quantitative Calibration Methods and the Extraction of Qualitative Information:, Anal. Chem., 60, 1193–1202, 1988. The use of PLS and other multivariate calibration techniques in noninvasive analysis of arterial blood gases is discussed in the Thomas et al. patent, supra.

Figure 4:
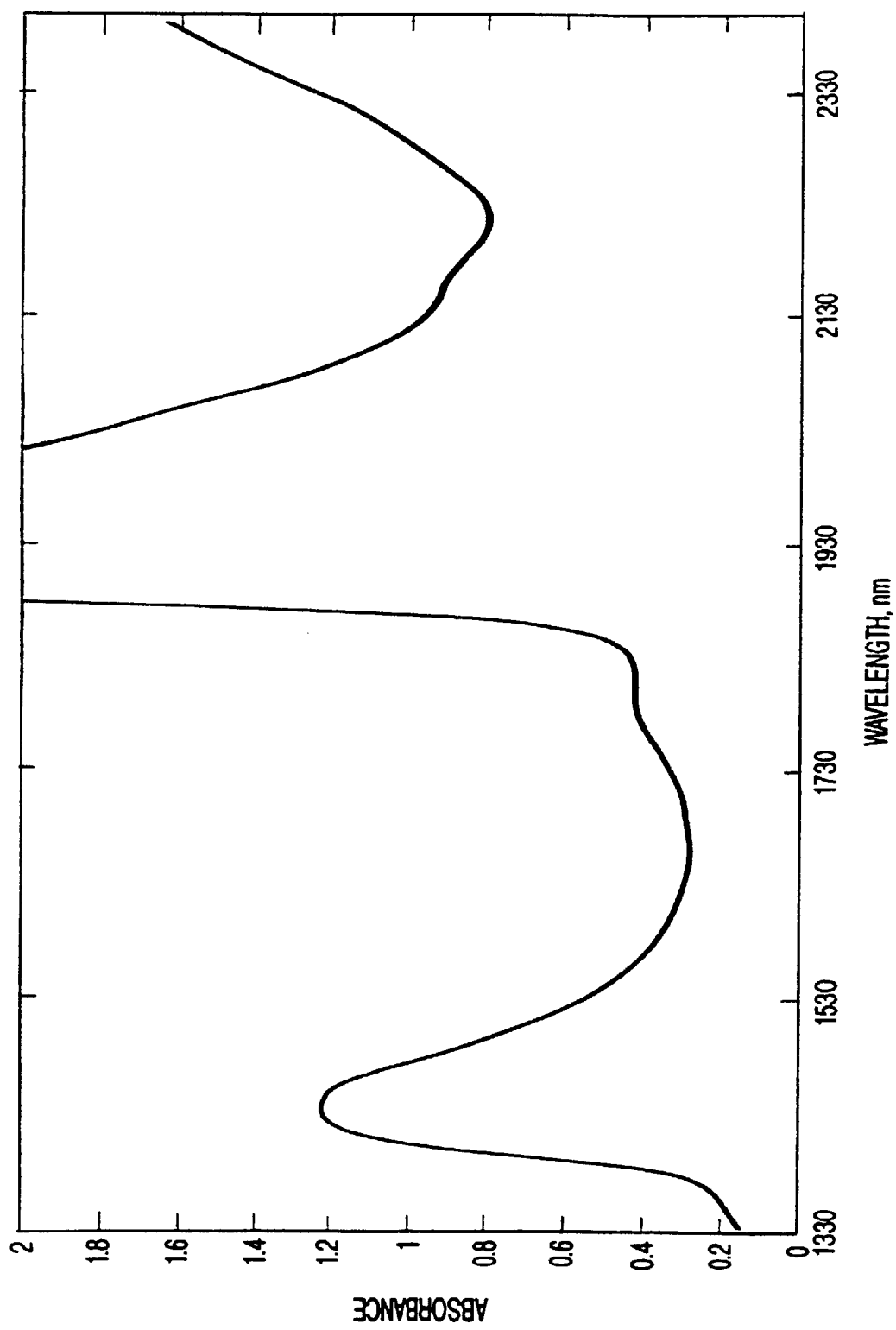
FIG. 4 is a graph of absorbance v. wavelength (nm) for thirty-nine spectra of lysed blood solutions at varying pH, [$HCO_3-$] and $O_2$ sat., wherein the primary absorbances seen are those from water combination bands.
Figure 5:
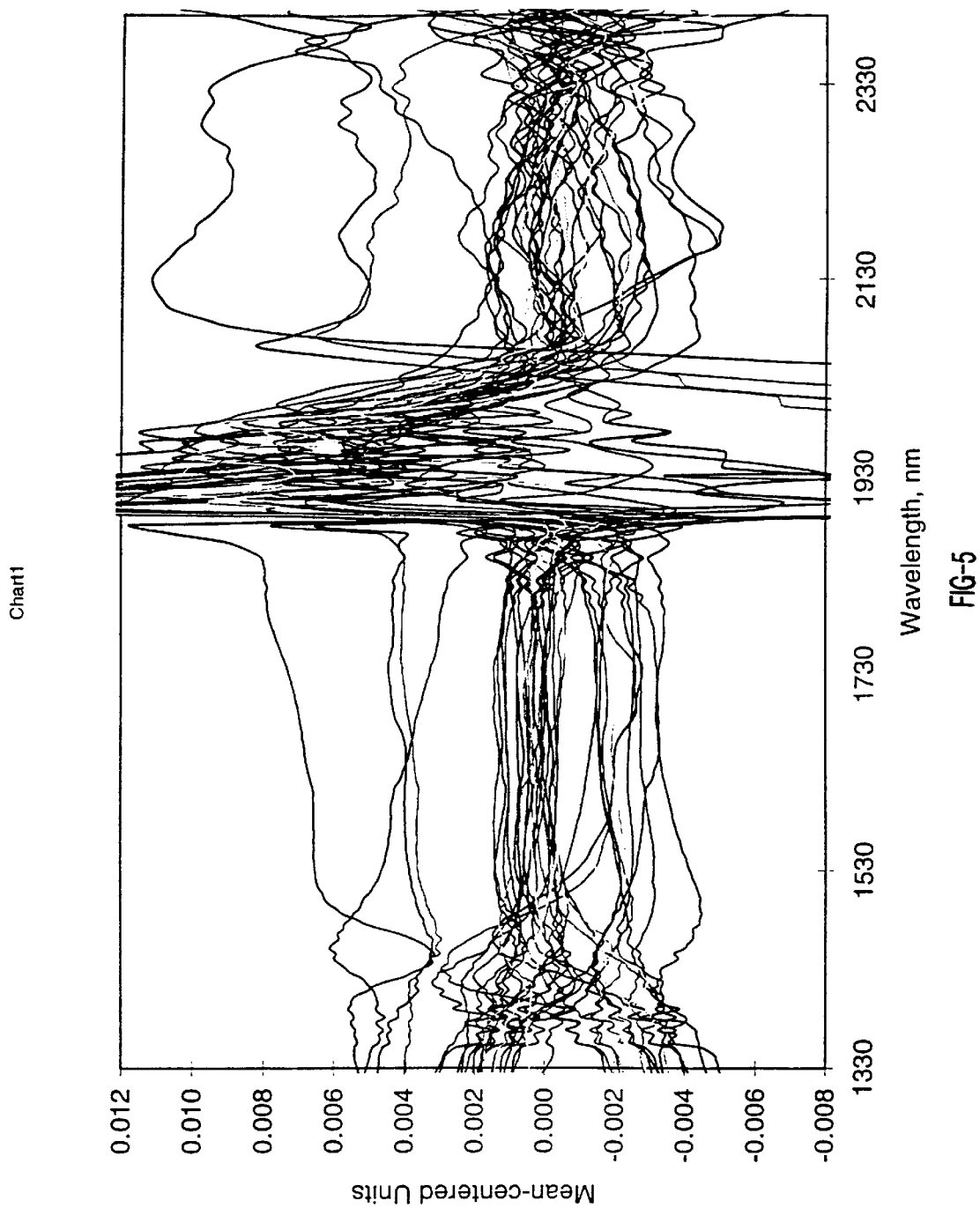
FIG. 5 is a graph of the mean-centered spectral data for the thirty-nine lysed blood solutions, whose spectra are illustrated in FIG. 4.

FIG. 4 illustrates the spectra obtained from the 39 lysed blood solutions identified above at varying pH, [$HCO_3^-$] and $O_2$ sat. The primary absorbances seen are these from water combination bands (i.e., 1420 and 1914 nm). The 39 spectra used for analysis from the lysed blood experiment are shown in FIGS. 4 and 5 as, respectively, absorbance data and mean centered absorbance data. Spectral variation due to pH changes are within the line widths of the individual spectra when the data are displayed as absorbance in FIG. 4. Primary absorbances at 1420 nm and 1914 nm in FIG. 4 are due to combination bands of water, $v_1+v_3$ and $v_2+v_3$ respectively, where $v_1$ refers to the symmetric stretching, $v_2$ the bending and $v_3$ the antisymmetric stretching mode. See, K. Buijs and G. R. Choppin, "Near-infrared Studies of the Structure of Water I. Pure Water", J. Chem. Phys., 39, 2035–2041, 1963. No discernible bands from species other than water are seen within the mean centered data.

PLS modeling, as explained in D. M. Haaland and E. V. Thomas, "Partial Least Squares Methods for Spectral Analyses. 1. Relation to Other Quantitative Calibration Methods and the Extraction of Qualitative Information", Anal. Chem., 60, 1193–1202, 1988, aided not only in developing quantitative models for pH, but also as a tool for discerning the location of information related to pH. Several spectral subregions (chosen based on the known location of carbon-hydrogen and nitrogen-hydrogen bands) were used as input into the PLS software. The 1820–2040 nm region was removed because of high water absorbance, resulting in low signal to noise. Summary results are shown in Table 1.

TABLE 1

PLS Results for Lysed Blood Spectra

| Spectral Region, nm | Number of Optimum PLS Factors | Cross Validated Standard Error of Prediction, pH units | $R^2$ |
|---|---|---|---|
| 1300–2380 | 5 | 0.175 | 0.506 |
| 2040–2380 | 5 | 0.185 | 0.445 |
| 1500–1820 | 13 | 0.037 | 0.978 |

Figure 3:
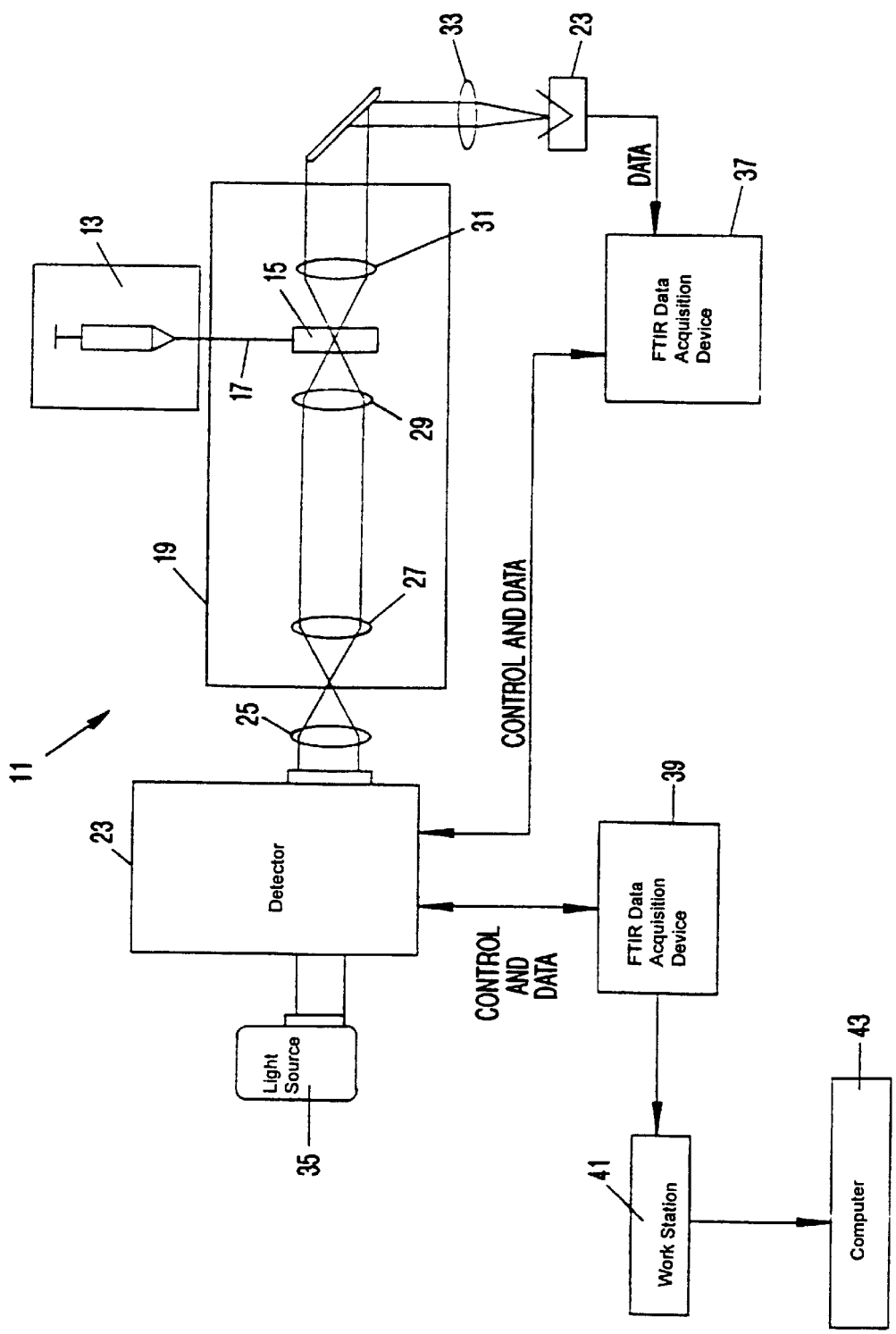
FIG. 3 is a diagram of the flow system used for the spectral analysis of lysed blood and blood plasma.
Figure 6:
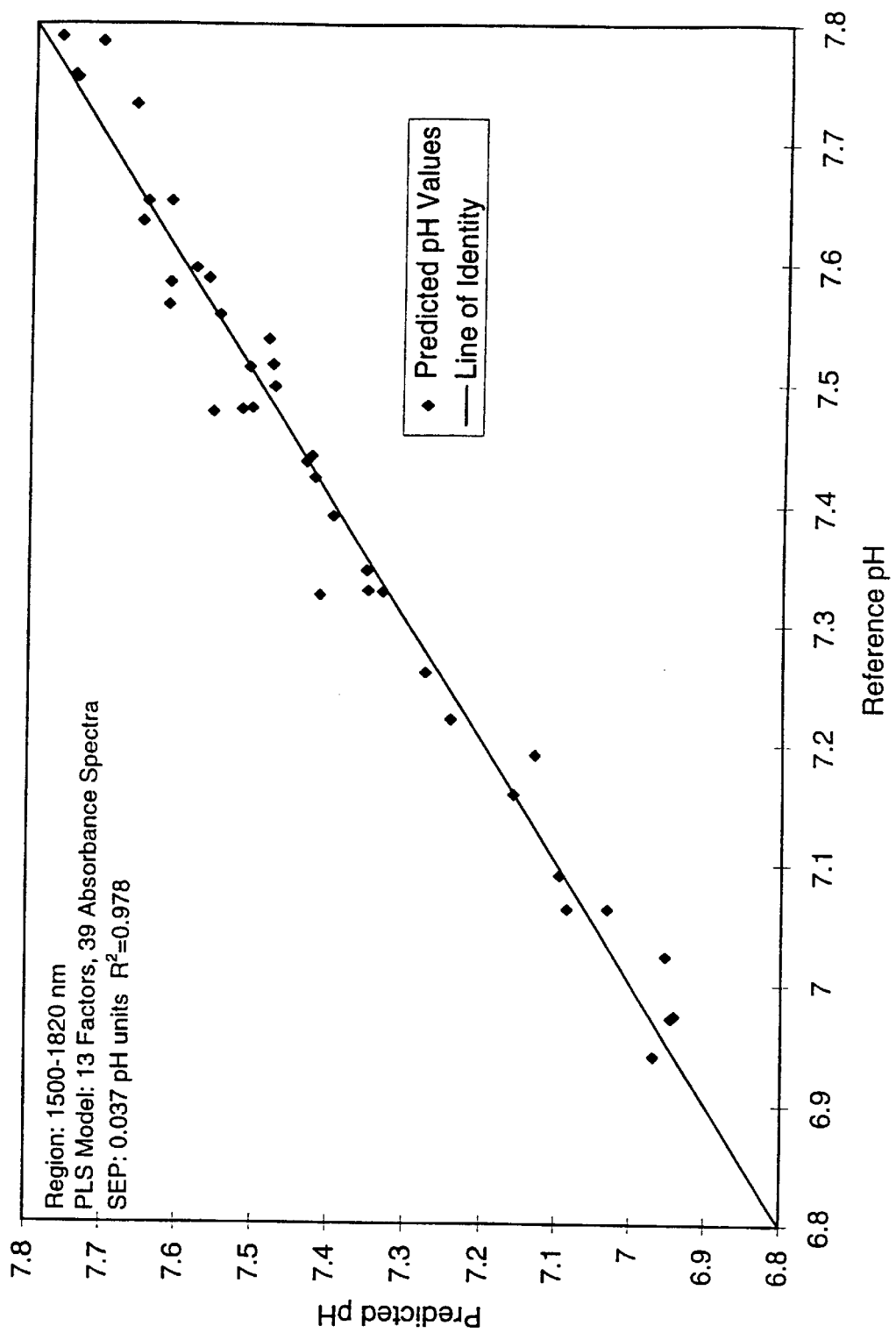
FIG. 6 is a graph representing the correlation between reference pH (determined by conventional wet chemistry) v. predicted pH values using PLS modeling in the 1500–1820 nm range.

With the instrumentation of FIG. 3, only one of the three spectral regions identified in Table 1 provided clinically useful calibration models (i.e., using the data between the main water absorbances (i.e., 1420 and 1914 nm) and PLS modeling provided the best calibration model with a cross-validated standard error of prediction of 0.037 pH units). Clinically useful being defined as SEP values less than 0.05 pH units. The results from the 1500–1820 nm region are illustrated in FIG. 6, in which the reference pH values (obtained, as indicated above, with the Corning 288 automated blood gas analyzer) are plotted against the predicted pH values using PLS modeling. Information located between the water bands is primarily associated with carbon-hydrogen and nitrogen-hydrogen moieties, suggesting that variation in protein bands is providing the source of the information for the pH model.

With the set up illustrated in FIG. 3, only the model for the 1500–1820 nm region is clinically useful. The present data for the 2040–2380 nm region does not provide a PLS model as strong as the model created for 1500–1820 nm, primarily due to the increased noise from the instrumentation used in acquiring the data. However, since the 2040–2380 nm region has similar overtones and combination bands, with different instrumentation clinically useful models can be developed for all regions identified in Table 1.

Figure 7:
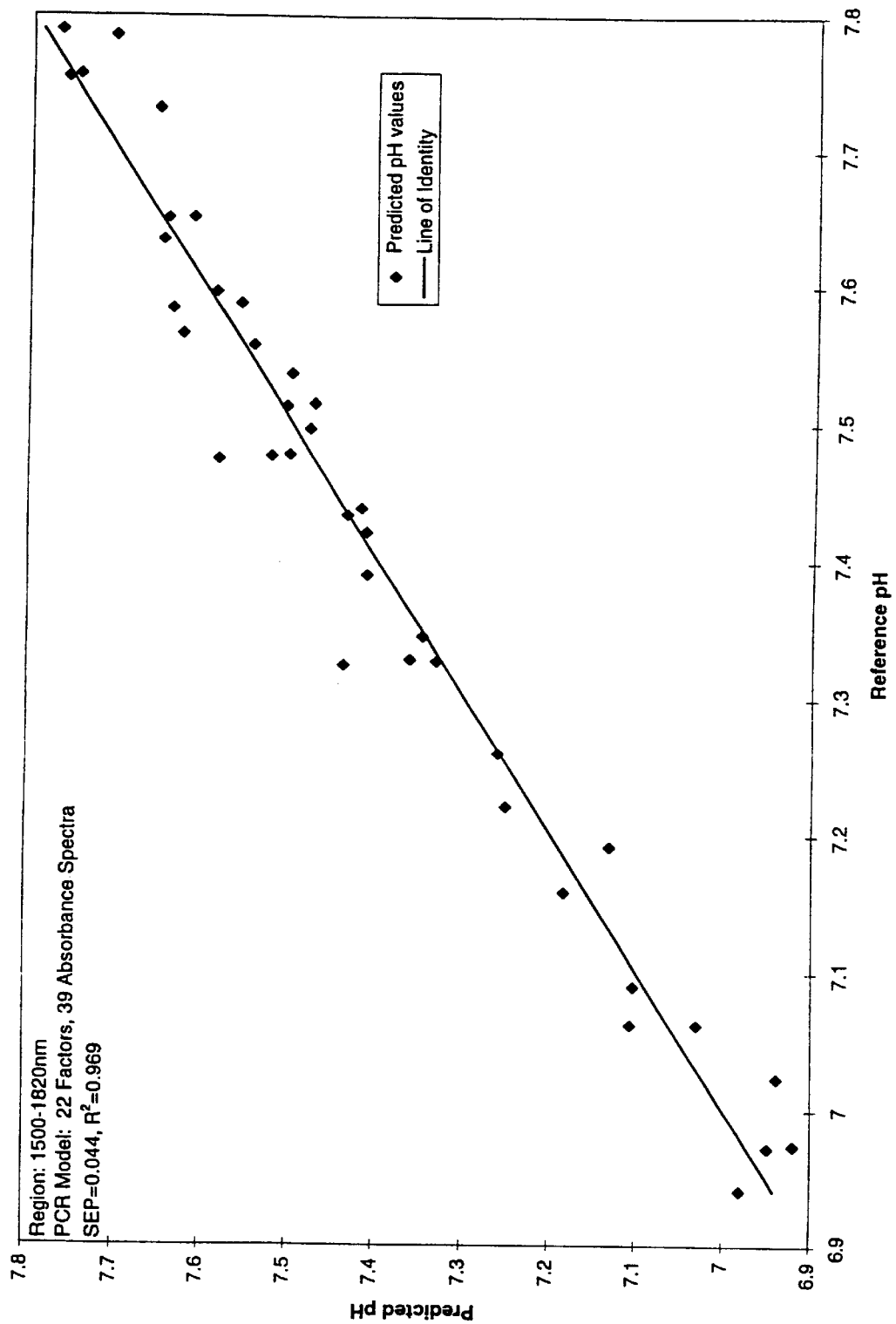
FIG. 7 is a graph representing the correlation between reference pH (determined by conventional wet chemistry) v. predicted pH values using PCR modeling in the 1500–1820 nm range.

In addition to PLS modeling as discussed above, other multivariate methods (e.g. PCR, PLS2, CLS, Q-matrix, ridge regression, cross-correlation, Kalman filtering, MLR, neural networks, and continuum methods are expected to provide comparable SEP values. For example, PCR modeling of the same data from the 1500–1820 nm region is illustrated in FIG. 7. The reference pH values plotted are the same as those used in FIG. 6.

Figure 8:
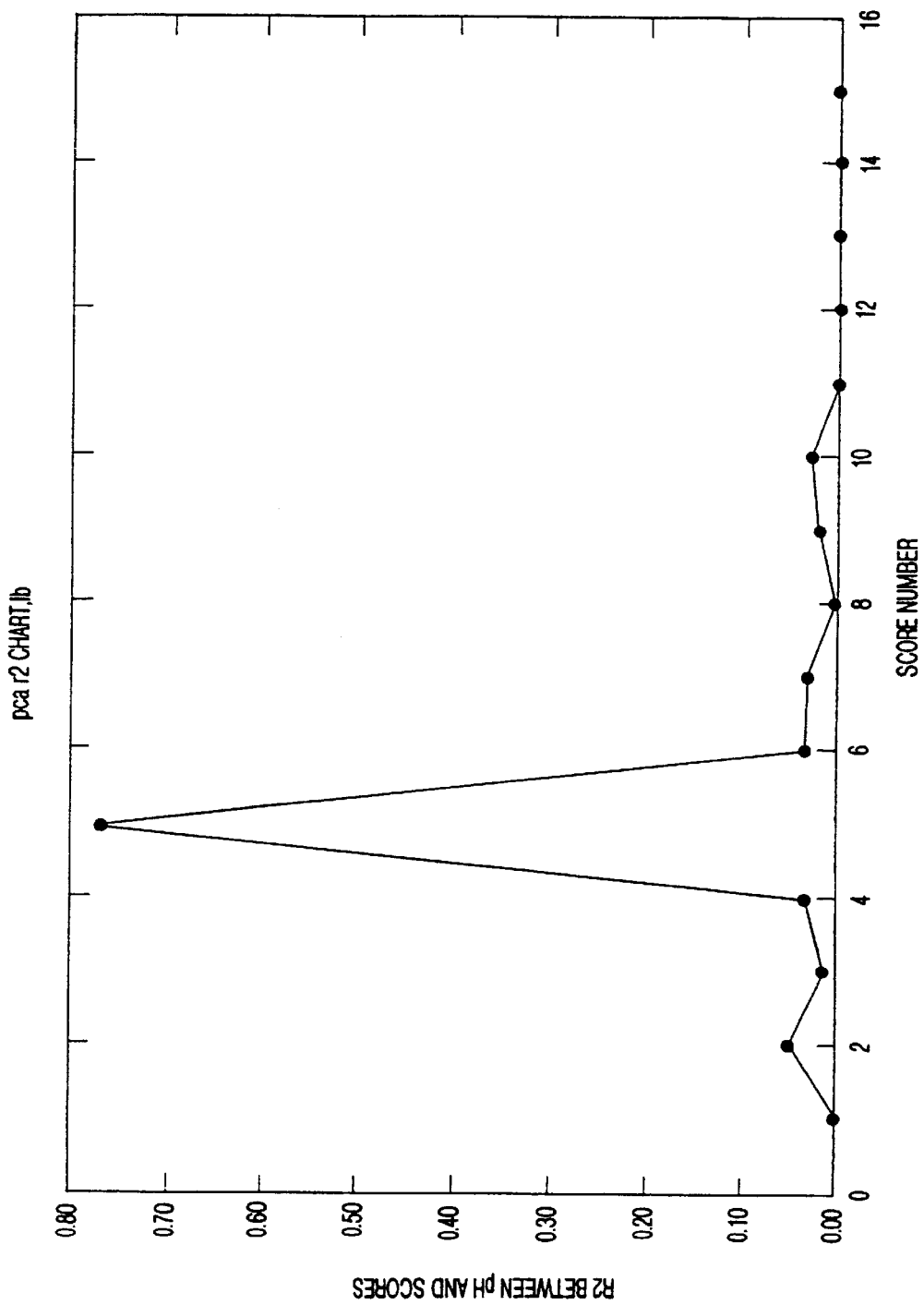
FIG. 8 is a graph illustrating the relationship between the squared correlation coefficient calculated between reference pH values and principle component analysis (PCA) scores, with the absorbance data collected from titrated lysed blood in the 1500–1820 nm range.
Figure 9:
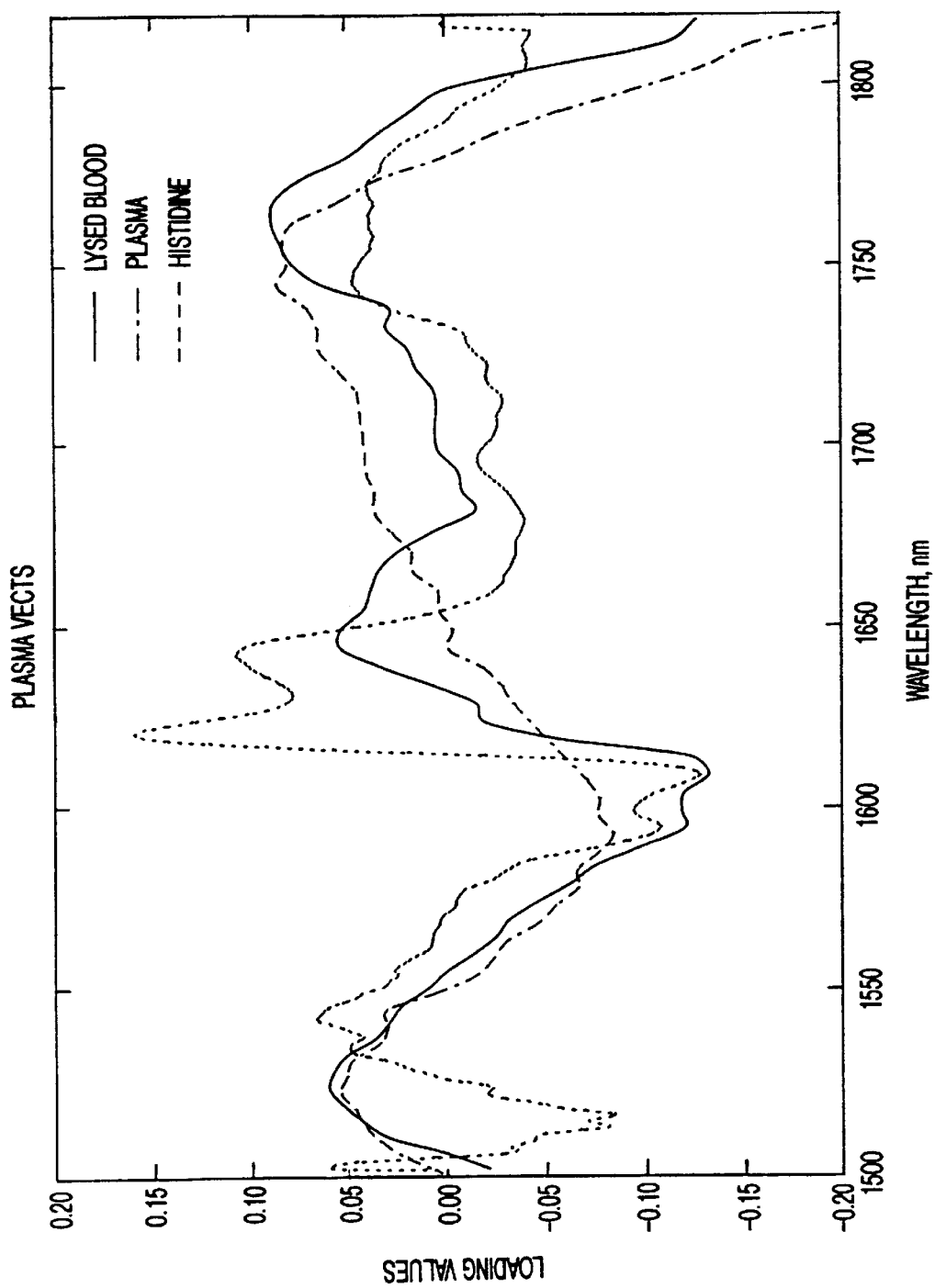
FIG. 9 is a graph illustrating loading vectors v. wavelength (nm) for loading vector (5 for lysed blood) whose score best correlated to pH from spectral data collected from lysed blood, histidine, and plasma solutions.

In order to determine the source of the pH information obtained from the lysed blood, PCA (principle component analysis) analysis was performed using the lysed blood spectral data. PCA analysis decomposes the spectral data into linear independent vectors, orthogonal to one another. This decomposition is done such that the maximum variance in the data is placed in the first loading vector. Each loading vector has associated with it a set of scores, one score for each sample. The score value for a sample represents the amount of the corresponding loading vector contained in the sample spectrum. The scores from each loading vector were compared to the reference pH values. The squared correlation coefficient ($R^2$) was calculated between each set of scores and pH and plotted. The results are illustrated in FIG. 8 where, for the 1500–1820 nm region, the squared correlation coefficient ($R^2$) calculated between reference pH values is plotted against eigenvector scores. The eigenvector that provided scores giving the largest correlation coefficient was examined and compared to those from other data sets. As seen in FIG. 8, the scores of eigenvector 5 provide the highest correlation coefficient to pH. Eigenvector 5 from the lysed blood data is shown in FIG. 9. Upon examination of FIG. 9, prominent variation is noted in the eigenvector at 1600 nm. The variation at 1600 nm is consistent with variation C—H or N—H overtones, possibly associated with variation in amino acid or protein structure.

With reference to FIG. 9, a likely source of the variation seen at 1600 nm in the lysed blood data is the amino acid histidine. Within the important physiological pH range of 6.8–7.8, the most important ionizable amino acid is histidine. See, J. E. Sherwin and B. B. Bruegger, *Clinical Chemistry, Theory, Analysis and Correlation*, 388–402, C. V. Mosby, St. Louis, 1984. The pK (i.e., the pH at which the concentration of the acidic form of the molecule is equal to the concentration of the basic form of the molecule) of the free amino acid is 5.97, however when bound, the pK can vary. The ionization occurring between pH 6.8 and 7.8 is:

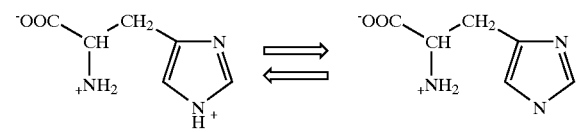

In whole blood, the primary buffer (i.e., that hemoglobin which is able to absorb more hydroxyl and hydrogen ions than any other chemical species in blood and not change the pH) is the hemoglobin molecule. The buffering capacity of hemoglobin is determined by its histidine. Of the 36 histidyl within the hemoglobin structure, 22 of these are titratable. See, C. Ho and I. M. Russu, "How Much Do We Know about the Bohr Effect of hemoglobin?", Biochemistry, 26, 6299–6305, 1987. The spectra from the titrated histidine solutions were examined by PLS as well as PCA and the results were compared to those from lysed blood.

Also shown in FIG. 9 is the eigenvector best correlated to pH as calculated from the histidine spectra obtained from the set of 200 mmol/L solutions described above. There are features common to both eigenvectors. In particular, similar variations at 1600 nm are seen. Chemically, the transition occurring in the histidine molecule involves primarily the N—H bond as the histidine is titrated. However, it is known that the neighboring C—H bonds of the heterocycle are affected as well. See C. T. Craescu, C. Schaeffer, J. Mispelter, J. Garin and J. Rosa, Journal of Biological Chemistry, 261, 7894, 1986. Thus the variation seen in the eigenvector could be due to the C-2 or C-4 protons or perhaps a combination of those and the N—H overtones.

In order to determine if the pH variation seen in the lysed blood spectra is derived from primarily histidine from hemoglobin or from histidine in other proteins, plasma protein solutions were examined. PLS modeling was performed using the resulting spectra. Models were established, but the quantitative precision of the PLS model for pH in plasma is poor. Standard errors of predictions for the spectral region 1300–2500 nm were no greater than $R^2=0.590$ and SEP=0.231. A table showing the results is below:

TABLE 2

| Spectral Region, nm | Number of Optimum PLS Factors | Cross Validated Standard Error of Prediction, pH units | $R^2$ |
| --- | --- | --- | --- |
| 1300–2380 | 6 | 0.259 | 0.483 |
| 2040–2380 | 1 | 0.333 | 0.146 |
| 1500–1820 | 6 | 0.231 | 0.590 |

Compared with the data set forth in Table 1 this finding suggests that plasma proteins do not contribute significantly to the pH model developed for the lysed blood data. Further evidence of this was obtained from the PCA analysis of the spectral data, analogous to that performed on the lysed blood and histidine spectral data as discussed above. Though not illustrated no single set of scores provided a squared correlation coefficient greater than 0.40. The eigenvector for lysed blood (number 5) best correlated to pH ($R^2 \cong 0.8$) is shown overlaid with those from the histidine (vector number 2) and plasma solutions (vector number 4) in FIG. 9.

A general shape seen in the plasma eigenvector that mimics the histidine and lysed blood eigenvectors can be seen, suggesting that similar chemistry may be present in the plasma solutions, but the variations are not strong enough to form a quantitative model. Titration data available for albumin, the largest constituent in plasma, confirm that over the 5–8 pH range very little buffering capacity is present. See C. Tanford, S. A. Swanson and W. S. Shore, "Hydrogen Ion Equilibria of Bovin Serum Albumin:, J. Amer. Chem. Soc., 77, 6414–6420, 1955.

Given the fact that absorbance bands in the near infrared are overtones and combinations of fundamental absorbance bands, near infrared bands, arising from the same fundamental mode can occur at various locations throughout the 500–2500 nm region. Thus, the histidine bands present at 1600 nm are expected to appear at other locations. Indeed, previous work has shown bands from histidine appearing between 2040 nm and 2380 nm, namely, 2060–2115 nm, 2160 nm, 2225–2235 nm and 2360 nm. See, Mary K. Phelan, Investigations of Quilibrium Conditions Using Near Infrared Spectroscopy, (1990) (unpublished Ph.D disseration, University of Washington). As discussed above, the 2040–2380 nm region contains histidine information, however the instrumental system used in acquiring the data did not allow full recovery of the signal.

Figure 10:
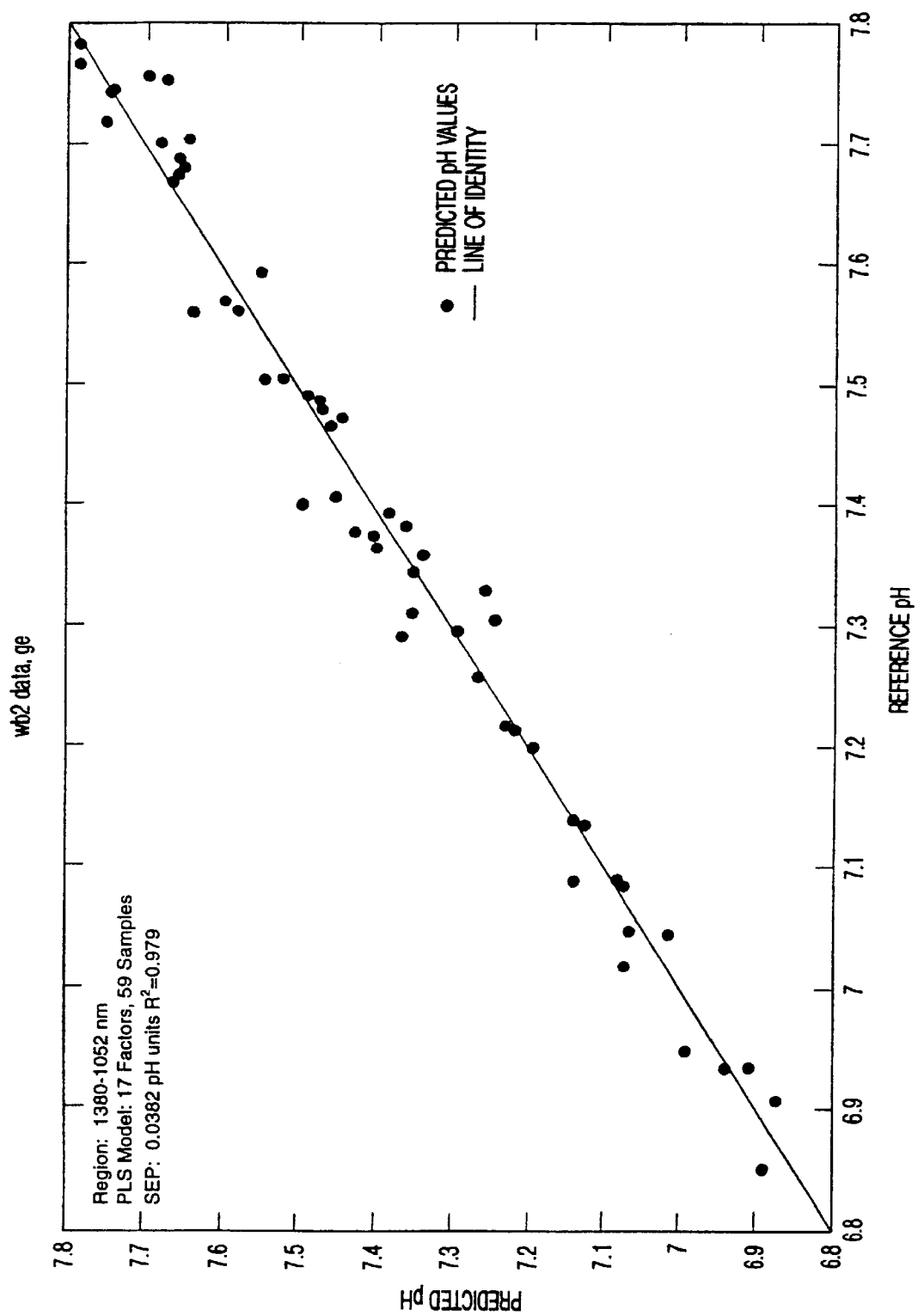
FIG. 10 is a graph representing the correlation between pH (determined by conventional wet chemistry) v. predicted pH values using PLS Modeling in the 1000–1300 nm region.
Figure 11:
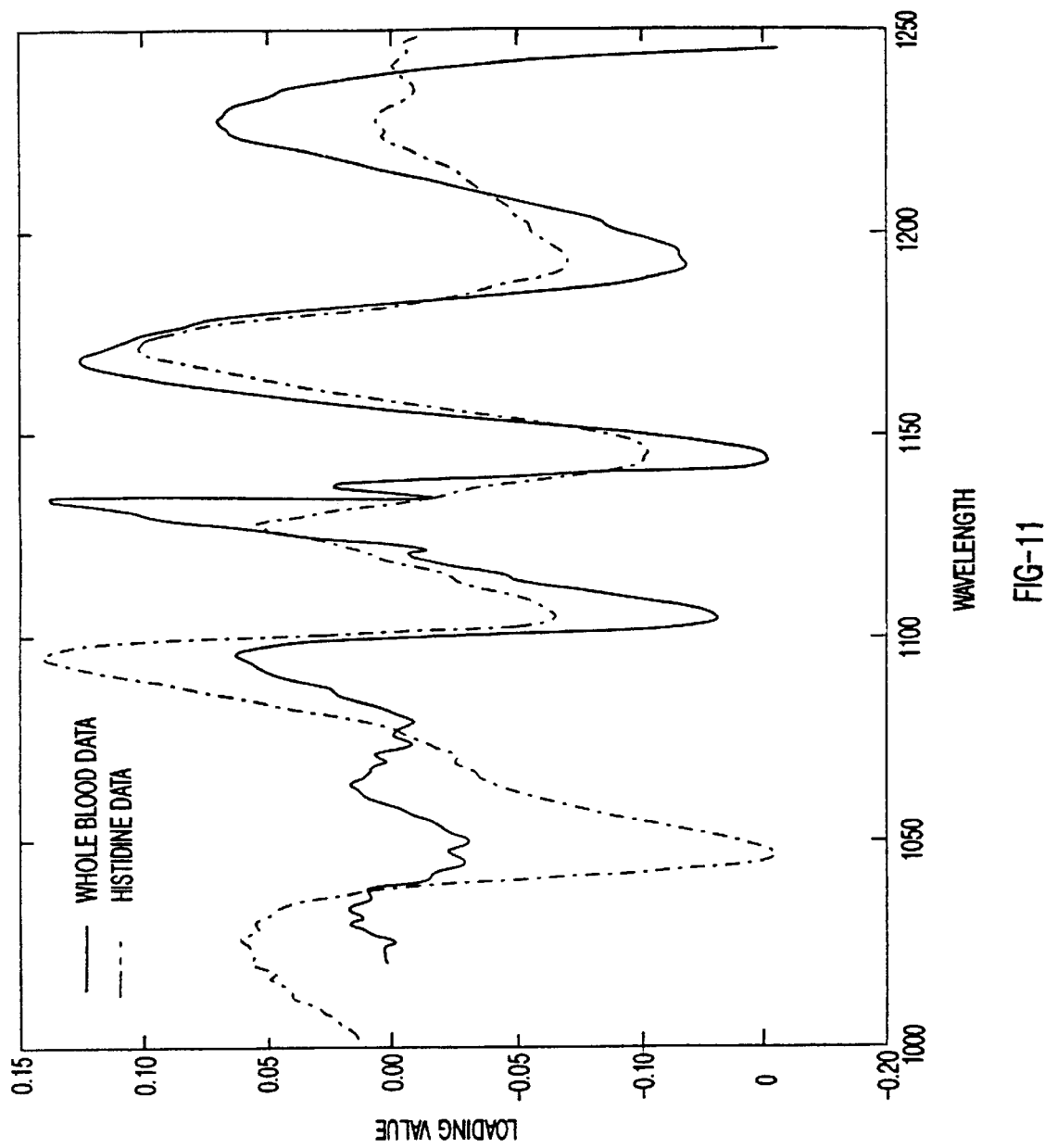
FIG. 11 is a graph illustrating loading vectors v. wavelength (nm) for the loading vector whose score best correlated to pH from spectral data for whole blood and histidine solutions.

To demonstrate that pH can be measured within the wavelength region 1000–1300 nm, data was collected from whole blood static samples with instrumentation (not shown) including a Perkin Elmer-2000 FT-NIR equipped with a 5 mm Ge liquid nitrogen cooled detector, and a 10 mm pathlength cuvette. Separate models were prepared for the regions 1000–1300 and 1500–1820 primarily due to differences in optimal pathlength for each region. The 1000–1300 nm region contains histidine bands which are much weaker than the 1500–1820 nm bands, thus allowing a longer pathlength to be used when acquiring data. In addition, one detector system is not sensitive to both regions simultaneously, and in fact, for the present data, two different detectors were used to acquire data from each of the regions. PLS modeling using data from the 1000–1300 nm data provided results comparable to those obtained with 1500–1820 nm, in particular, the SEP using the 1000–1300 nm data was 0.038 with an $R^2=0.978$. The results are illustrated in FIG. 10, in which reference values (obtained by conventional wet chemistry) are plotted against the predicted pH values using PLS modeling. PCA analysis was also performed using the 1000–1300 nm data collected and compared to data collected from histidine solutions (prepared in the manner previously indicated) from the same frequency region. The loading vectors whose scores provided the largest $R^2$ to measured pH are shown in FIG. 11. Comparable variations are seen in the loading vectors, again suggesting that the spectral signature which correlated to pH is from histidine.

Figure 12:
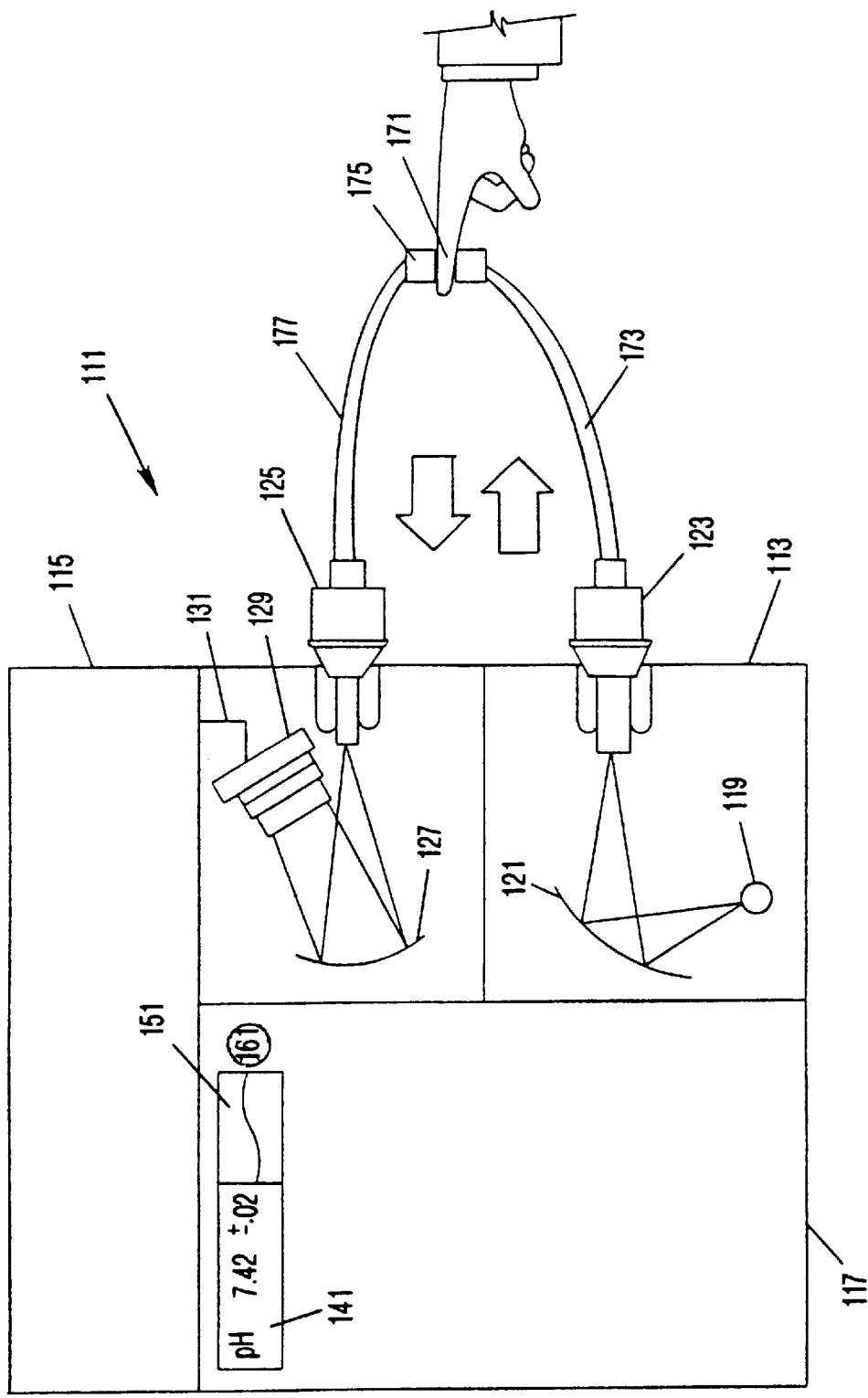
FIG. 12 is a schematic illustration of the preferred embodiment of the apparatus of the present invention.

With reference to FIG. 12, the preferred noninvasive pH monitor 111 of the present invention includes a spectrometer 113, an electronics and computer processing module 115, and a visual display module 117. Spectrometer 113 includes a broad band tungsten halogen light source 119, a focusing mirror 121, a fiber optic interface 123, a second fiber optic interface 125, a grating 127, an Insb array detector 129, and an electronic buss 131. Module 115, includes a computing unit which, in turn, contains a microprocessor, memory, the data preprocessing algorithms, the multivariate calibration model, the multivariate algorithm, and outlier detection algorithms. Visual display module 117 includes a pH display 141. As illustrated, display 141 includes a determination and the estimated uncertainty of such determination. Also included in module 117 are a pH trend display 151 and a light 161 to indicate if the pH which has just been determined is an outlier.

To transmit light from spectrometer 113 to the fingertip 171 of the patient being monitored, monitor 111 includes a source fiber optic bundle 173, which terminates at finger/fiber device 175. Receiving fiber optic 177 returns the light from finger/fiber holder 175 to fiber optic interface 125. Finger/fiber holder 175 allows transmission through finger 171 and allows for adequate holding of the finger.

In operation, source 119 emits selected frequencies from approximately 1000–2500 nm. This light is focused on the end of fiber optic 173 held in interface 123 via focusing mirror 121 and then transmitted via source fiber 173 to illuminate the tissue, bone, nail and blood in fingertip 171. The portion of the light which is transmitted through fingertip 171 is them returned to spectrometer 113 by fiber bundle 177. The returning light is then separated into various wavelengths and detected by the array detector 129, capable of detecting at least some of the wavelengths of light between 1300 to 2400 nm. For the frequency range 1000–1300 nm it is preferred to use an InGaAs detector, otherwise the apparatus is the same.

The reflected light intensities at the various frequencies are then analyzed by the microprocessor of module 115, employing a multivariate algorithm (preferably PLS) utilizing several wavelengths from various regions of the entire spectral range of the transmitted light.

For invasive monitoring, a system based on the apparatus of FIG. 3 or such as described in reference to FIG. 50 in Thomas, et al. (insofar as it relates to pH monitoring), could be utilized.

Monitoring can also be made in the blood pulse mode as described in U.S. Pat. No. 5,355,880 to Thomas et al., all of which is incorporated by reference, including FIGS. 1 and 2 and column 17, line 9 to column 19, line 13, and claims 31–41. In blood pulse mode, spectra are acquired throughout the cardiac cycle of the patient. The resulting spectral data are analyzed to establish which spectra correspond with maximum concentration of blood (or maximum dilation) in the arterial system of the patient, and which spectra correspond with minimum concentration (or minimum dilation) of the arterial system. The spectra associated with minimum dilation will contain information regarding blood, skin, bone, and tissue. The spectra associated with maximum dilation will contain the same information plus an additional amount of blood information. To determine optical pulse pressure, the spectral difference at the isobestic frequency is calculated. Absorbance by wavelengths in the region from 800 to 810 nm are not strongly influenced by changes in oxygen saturation and are proportional to the amount of hemoglobin present. Thus, a plot of the average value between 800–810 nm will show the variation in hemoglobin concentration. The magnitude of this difference will correspond to the spectral difference between the systolic and diastolic pulses. This spectral difference is, in turn, a general measure of the quality of the spectral data. Those spectra having an abnormal optical pulse pressure are trimmed (i.e., removed) prior to further analysis. The trim process removes spectra which deviate significantly from the norm due to motion of the patient or other artifacts. As some of these artifacts will influence the spectra in an adverse manner, the removal of these spectra is important for production of an accurate pulse monitor. Additional preprocessing of the data may be required due to specific operating conditions. The calculation of the "additional" blood spectrum can be performed by several methodologies, including subtraction of the appropriately transformed spectral data from the maximum and minimum dilation. The above process effectively removes the interfering background and provides the multivariate algorithm with a spectrum corresponding to the additional blood. The resulting additional blood or pulse blood spectra may be subsequently averaged with existing scans to improve the signal-to-noise ratio of the spectrum to be analyzed. The resulting spectrum is then analyzed by the multivariate algorithm contained module 15 (FIG. 1 of Thomas, et al.). In the preferred embodiment the algorithm employed would be partial least squares or neural networks. The algorithm will either measure directly or calculate pH. The instrument will display the current value of pH, the uncertainty as well as the past history of such parameter, as explained with regard to the tissue mode. The accuracy of each determination will also be assessed through the use of outlier detection methods contained in the computing unit in module 15 of FIG. 1 of Thomas, et al.). In the blood pulse mode, the tissue/pulse mode switch 60, FIG. 1 of Thomas, et al., is set for the blood pulse mode.

Whereas the drawings and accompanying description have shown and described the preferred embodiment of the present invention, it should be apparent to those skilled in the art that various changes may be made in the form of the invention without affecting the scope thereof.

We claim:

1. A method of determining pH in pulsatile blood in a human utilizing spectra which contains histidine information, said method comprising steps of:
   a) generating light including three or more different wavelengths which exhibit attenuation due to histidine, said wavelengths being in the near infrared range;
   b) irradiating blood containing tissue with said wavelengths so that there is attenuation of at least some intensities of said wavelengths, said attenuation being a function of said blood containing tissue, including histidine in said blood containing tissue;
   c) measuring at least a portion of said some intensities of said wavelengths emerging from said blood containing tissue;
   d) using the presence of blood pulsations in said blood containing tissue and said measured intensities to obtain blood related spectral information; and
   e) estimating the value of said blood pH from said blood related spectral information.

2. A quantitative analysis instrument for noninvasive spectroscopic measurement of pH in human tissue, said instrument comprising:
   a) a source including at least three different wavelengths of light which exhibit attenuation due to histidine, said wavelengths being in the near infrared range;
   b) optics for directing said wavelengths into said tissue;
   c) at least one detector for measuring the intensities of at least a portion of said wavelengths emerging from said tissue; and
   d) electronics for processing said measured intensities to estimate pH values; and
   e) means for indicating said estimated values of pH.

3. A method of determining noninvasively and in vivo, pH in arterial blood in a human utilizing spectra which contains histidine information, said method comprising steps of:
   a) generating light at three or more different wavelengths which exhibit attenuation due to histidine, said wavelengths being in the near infrared range;
   b) irradiating in vivo and noninvasively said arterial blood with said wavelengths, so that there is attenuation of at least some intensities of said wavelengths, said attenuation being a function of said arterial blood, including histidine in said arterial blood;
   c) measuring at least a portion of said some intensities of said wavelengths emerging from said arterial blood during the diastolic portion of the cardiac cycle of said human to obtain a diastolic set of at least three spectral intensities v. wavelengths, some of said wavelengths having some intensity attenuation due to histidine;
   d) measuring at least a portion of said some intensities of said wavelengths emerging from said arterial blood during the systolic portion of said cardiac cycle to obtain a systolic set of at least three spectral intensities v. wavelengths, some of said wavelengths having some intensity attenuation due to histidine;
   e) determining the measure of change between said diastolic and systolic sets of spectral intensities v. wavelengths; and f) estimating the value of pH in said arterial blood from said intensity attenuation due to histidine in said measure of change between said diastolic and systolic sets of spectral intensities v. wavelengths.

4. A method of determining pH in pulsatile blood utilizing spectra which contains histidine information, said method comprising steps of:
 a) irradiating blood containing tissue with wavelengths of light in the near infrared range which are attenuated by histidine, so that there is attenuation of at least some intensities of said wavelengths of said light, said attenuation being a function of said blood containing tissue, including histidine in said blood containing tissue;
 b) measuring at least a portion of said some intensities of said wavelengths of said light emerging from said blood containing tissue;
 c) using the presence of blood pulsations in said blood containing tissue and said measured intensities to obtain blood related information; and
 d) estimating the value of said blood pH from said blood related information.

5. The method of claim 4, wherein said step of irradiating is performed on pulsatile blood in a human.

6. A quantitative analysis instrument for noninvasive spectroscopic measurement of pH in tissue, said instrument comprising:
 a) a source of at least three different wavelengths of light which are attenuated by histidine, said wavelengths being in the near infrared range;
 b) optics for directing said wavelengths into said tissue;
 c) at least one detector for measuring the intensities of at least a portion of said wavelengths emerging from said tissue;
 d) electronics for processing said measured intensities to obtain tissue related information;
 e) electronics for processing said tissue related information to estimate pH values; and
 f) means for indicating said estimated values of pH.

7. A quantitative analysis instrument for noninvasive spectroscopic measurement of pH in tissue, said instrument comprising:
 a) a source of at least three different wavelengths of light which are attenuated by histidine, said wavelengths being in the near infrared range;
 b) means for directing said wavelengths into said tissue;
 c) at least one means for measuring the intensities of at least a portion of said wavelengths emerging from said tissue;
 d) means for processing said measured intensities to obtain tissue related information;
 e) means for processing said tissue related information to estimate pH values; and
 f) means for indicating said estimated values of pH.

8. A method of determining noninvasively and in vivo, pH in arterial blood utilizing spectra which contains histidine information, said method comprising steps of:
 a) irradiating in vivo and noninvasively said arterial blood with wavelengths of light in the near infrared range which exhibit attenuation due to histidine, so that there is attenuation of at least some intensities of said wavelengths of said light;
 b) measuring at least a portion of said some intensities of said wavelengths of said light emerging from said arterial blood during a portion of the cardiac cycle of said human to obtain spectral intensities;
 c) determining a measure of change in said spectral intensities; and
 d) estimating the values of pH in said arterial blood from said measure of change.

* * * * *